United States Patent [19]
Gysi

[11] Patent Number: 5,913,237
[45] Date of Patent: Jun. 15, 1999

[54] APPARATUS FOR PROVIDING A FLUID CONNECTION BETWEEN A FIXED FLUID COUPLING AND A MOVING CONTAINER

[75] Inventor: Peter Gysi, Bellikon, Switzerland

[73] Assignee: Elpatronic AG, Zug, Switzerland

[21] Appl. No.: 08/688,601

[22] Filed: Jul. 30, 1996

[30] Foreign Application Priority Data

Aug. 23, 1995 [CH] Switzerland ............................ 2402/95

[51] Int. Cl.⁶ .................................................. G01M 3/02
[52] U.S. Cl. ............................................ 73/41; 73/863.83
[58] Field of Search ...................... 73/41, 49.2, 863.31, 73/863.33, 863.83, 863.91, 863.92, 864.34, 864.81, 864.85; 198/339.1; 209/522, 523, 591; 141/129, 177–179

[56] References Cited

U.S. PATENT DOCUMENTS 3,826,126  7/1974  Yasuhiro ................................ 209/591
4,092,991  6/1978  Rohrs .
5,365,771  11/1994 Gysi et al. .

FOREIGN PATENT DOCUMENTS

0579952 A1  1/1994  European Pat. Off. .
U 2 004 852  8/1970  Germany .
A 41 37 912  5/1993  Germany .
U 9403641  2/1994  Germany .
0022887  2/1979  Japan ............................................ 73/41

*Primary Examiner*—Robert Raevis
*Attorney, Agent, or Firm*—McCormick, Paulding & Huber

[57] ABSTRACT

Above containers transported on a conveyor, the apparatus is provided with a continuous revolving belt, which has perforations. These are in communication via passageways with fixed fluid couplings and the drive to the belt is set so that they move in step with the containers along the conveyor path. Thus, by simple means, a connection is provided between the moving containers and the fixed fluid couplings, and the system is suitable for high conveying speeds.

17 Claims, 5 Drawing Sheets

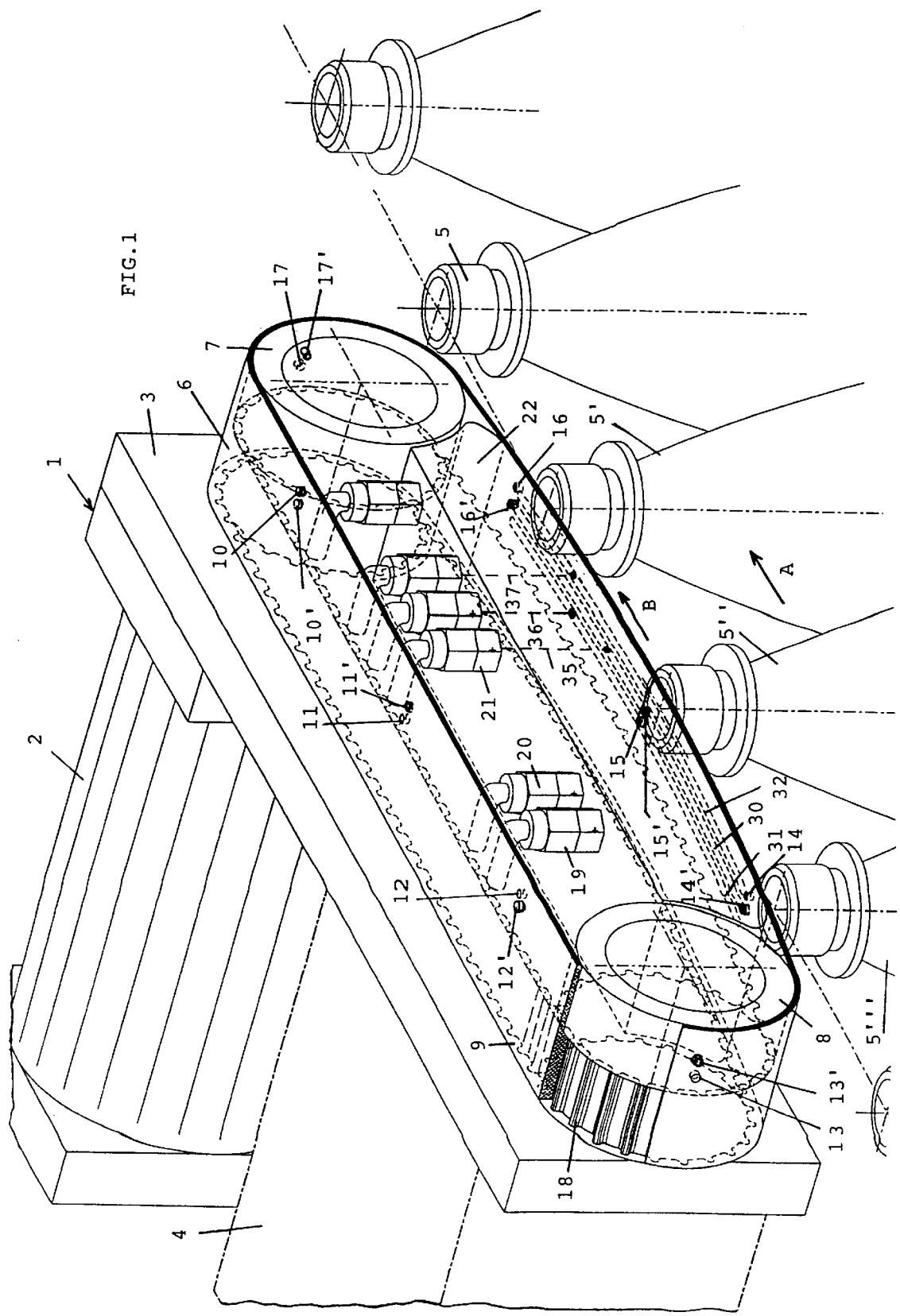

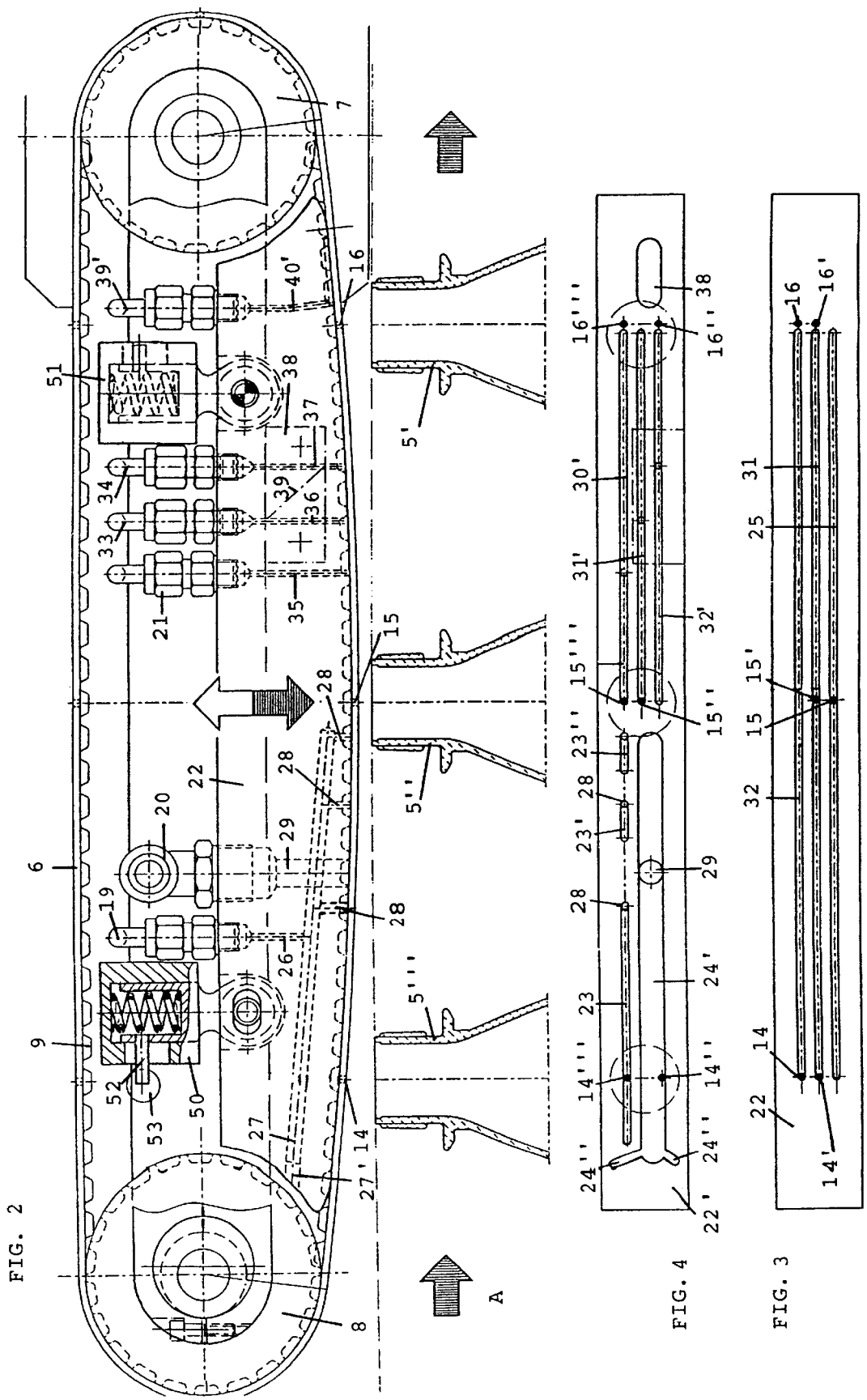

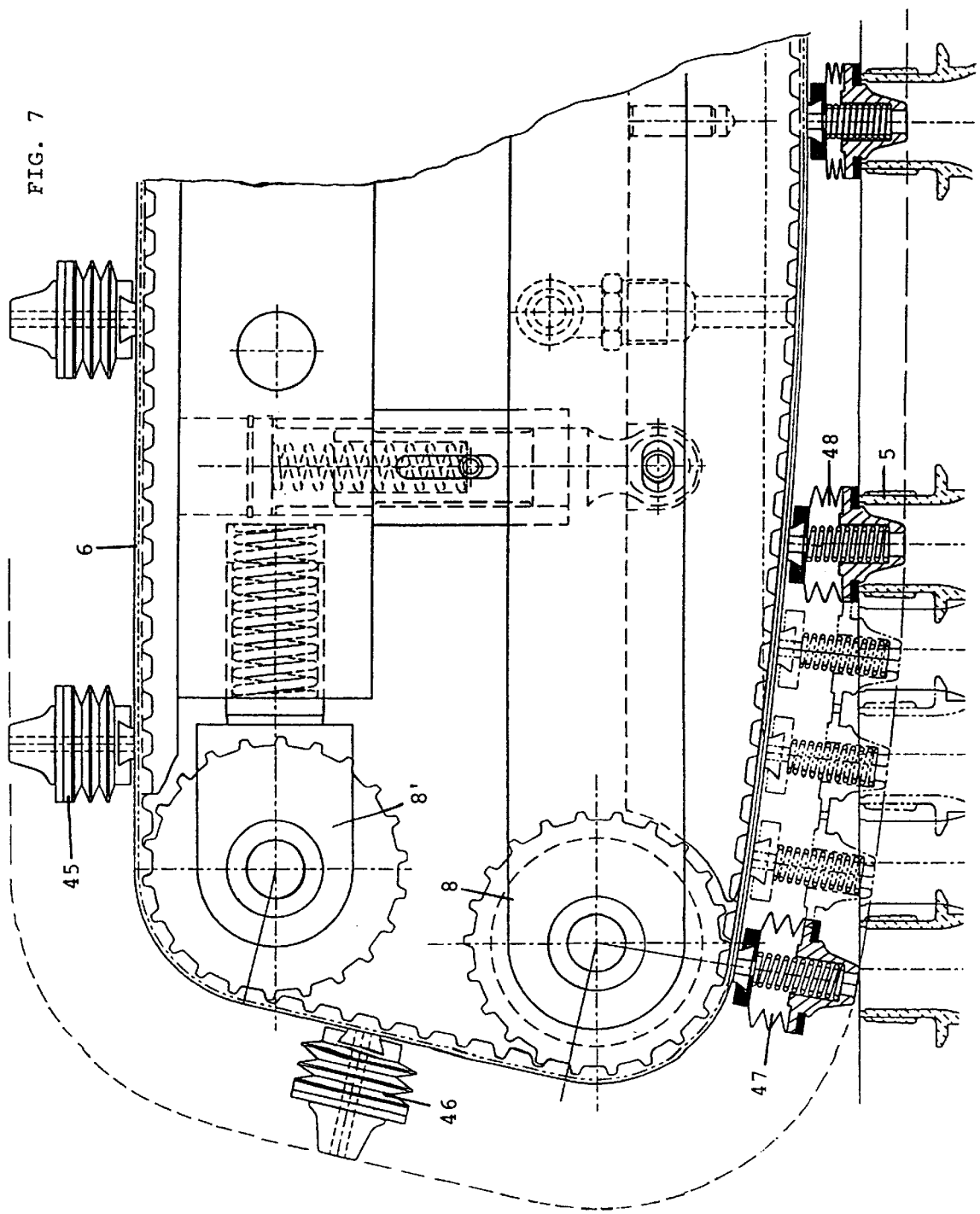

APPARATUS FOR PROVIDING A FLUID CONNECTION BETWEEN A FIXED FLUID COUPLING AND A MOVING CONTAINER

BACKGROUND OF THE INVENTION

The invention relates to an apparatus for providing a fluid connection between at least one fixed fluid coupling and at least one of a plurality of containers transported on a conveyor.

Such an apparatus, intended for the extraction of fluid in the inspection of bottles, is known from U.S. Pat. No. 5,365,771 having the same assignee. In that apparatus, gas samples are extracted from the bottles and fed to a fixed coupling at which an analysing instrument for the gas sample is provided. The bottles are transported on a carousel conveyor, which is expensive. An apparatus for inserting a fluid into a bottle for inspection purposes is moreover known from DE-U 9403641. This has an injection wheel arranged above the containers, which are conveyed in linear fashion. The injection wheel rotates above the conveyor line. Compared with the carousel, this does result in a simpler construction, but the duration of the connection, that is to say the time during which the fluid can be inserted into the bottle, is very short, especially at high container handling rates.

SUMMARY OF THE INVENTION

Therefore the object which lies at the basis of the invention is to provide an apparatus for making a fluid connection between a container which is being transported and a fixed fluid coupling, eg. a fixed coupling for feeding gas extracted from the container to an analysing device or a fixed coupling, for a fluid which is to be inserted into the container. This apparatus needs to be simple in its construction, and suitable for high container handling rates.

This object is achieved in a conveying system of the above-mentioned kind by providing a power-driven, essentially strip-like element, one side of which is in communication with the fluid coupling and the other side of which faces the container opening, and which has at least one perforation forming a connection between the fluid coupling and the container.

The provision of a strip-like element which can be driven so that it follows the containers as they are being transported affords the possibility both of simple construction and of extended period of contact between strip and container, as the length of the strip can be adopted accordingly.

The strip-like element can be unwound from a spool and discarded after it has been used once; this will happen mainly where the apparatus is used for handling containers affected by, or susceptible to, severe contamination, eg. in the chemical or pharmaceutical industry. In a particular embodiment, however, the strip-like element is in the form of an endless belt or band which, after establishing connection with a container, recirculates to establish connection with another container.

In one embodiment, the element runs on a guide element which preferably provides for both fluid feed to, and fluid discharge from it. However, the guide element may be dispensed with, particularly if the length of the strip-like element is not great.

BRIEF DESCRIPTION OF THE DRAWINGS

Embodiments of the invention will now be described in detail, by way of example, with reference to the drawings, in which:

FIG. 1 is a perspective view showing a series of bottles being conveyed together in an embodiment of the apparatus;

FIG. 2 is a partly sectioned side view of the apparatus of FIG. 1;

FIG. 3 is a view of the container side of a guide element;

FIG. 4 is a view of the container side of another guide element;

FIG. 7 is a partly sectioned side view of part of another embodiment of the apparatus.

DESCRIPTION OF THE PREFERRED EMBODIMENTS

Figure 5:
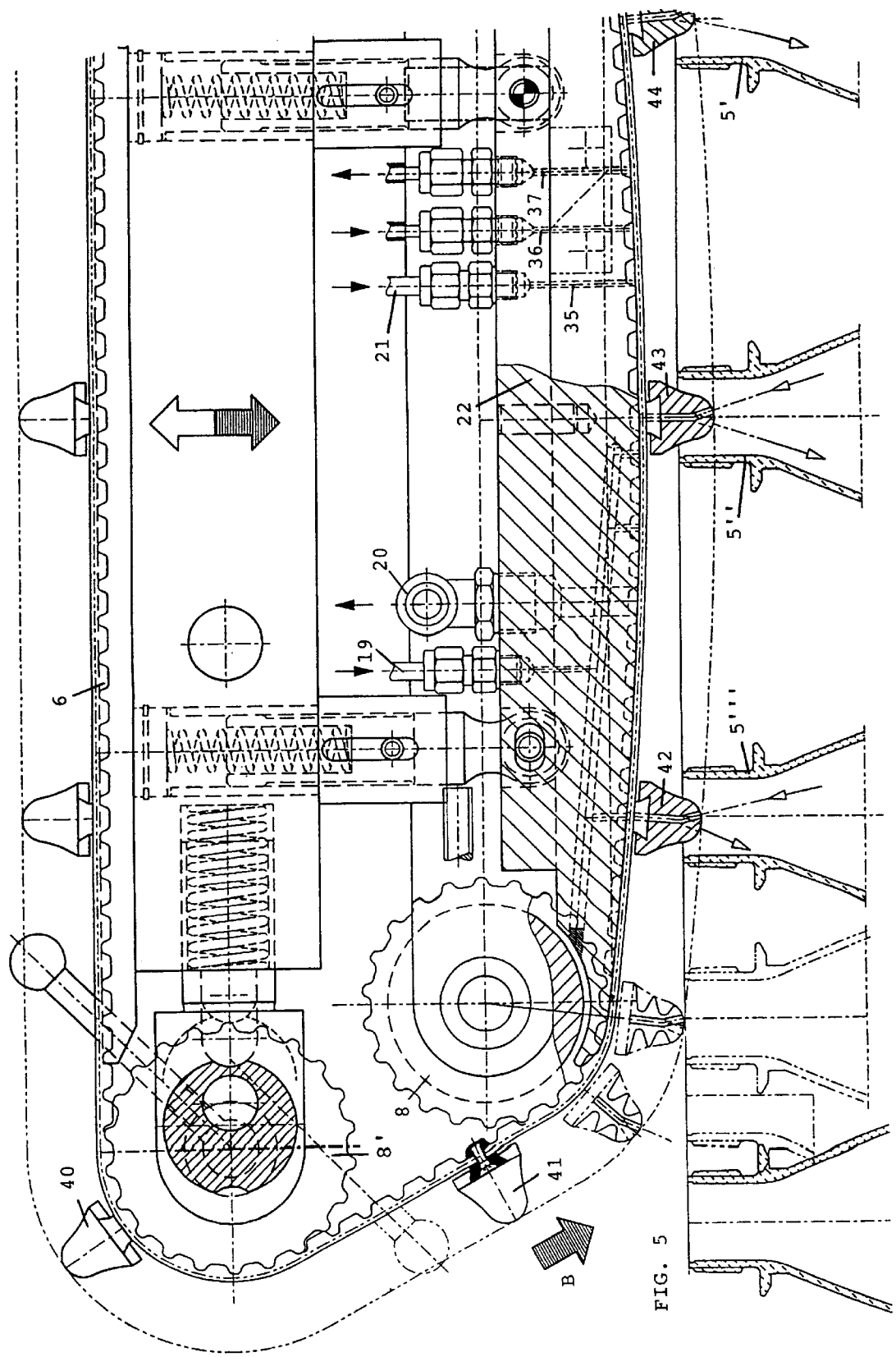
FIG. 5 is a partly sectioned side view of part of another embodiment of the apparatus.

FIG. 1 shows a first embodiment of the apparatus 1 in a schematic perspective view. A drive motor 2 and a coupling chest 4 for the fluid couplings (possibly also accommodating analytical devices) are carried on a support plate 3. The driven strip-like element 6, which in the example shown is an endless belt running around two guide pulleys 7 and 8, is provided on the front of the plate 3. The pulley 7 is driven by the electric motor 2 so that the speed of the belt between the guide pulleys can be adjusted to make it essentially equal to that of the containers or bottles 5,5', 5",5"', and so on (shown only in part) which are being conveyed in the direction of the arrow A. The drive to the belt can be effected eg. by profiling half of the belt as a toothed belt with teeth 9, and by providing the guide pulleys 7 and 8 with corresponding teeth 18 over part of their width. In the example shown, the element 6 is illustrated in the form of a flat strap, that is a belt with a rectangular cross-section. However, the cross-section of the belt or strip could of course also be square, round or elliptical.

A plurality of perforations 10,10' to 17,17' are provided in the belt. The spacing of these perforations is such that each perforation comes into register with a bottle mouth, as shown in FIG. 1 for the perforations 14,14',15,15' and 16,16', which are located over the mouths of the bottles 5'",5" and 5' respectively, in the position shown. Since the driving speed of the belt is selected so that the belt travels between the guide pulleys 7 and 8 at the same speed as the containers, each perforation in the belt travels in step with the container mouth assigned to it. Thus the perforation 14 together with the perforation 14' travels with the container 5'" from the guide pulley 8 to the guide pulley 7, remaining in contact with the container mouth throughout this period.

In order for a fluid connection to be made from a fixed coupling to the container via the respective perforation, the fluid has to be delivered to the individual perforation on the inside of the belt. In the example shown, a guide element 22 is provided for this purpose, and has, on a side facing the belt, passageways 30,31 and 32 which are in the form of grooves open towards the belt and extend along the direction of run of the belt. Each of these passageways is in communication with at least one fixed fluid coupling through ducts 35,36,37 in the belt guide element 22.

In the example shown, several fluid couplings are illustrated, with the fluid coupling 21 communicating with the passageway 30, the fluid coupling 33 communicating with the passageway 31 and the fluid coupling 34 communicating with the passageway 32 (see FIG. 2). These fluid couplings are fixed, and are connected, via pipes which run into the coupling chest 4, to corresponding sources of fluid or to analysing instruments. If the apparatus 1 is assumed to be an apparatus for extracting gas samples from containers for example, a compressed air source may be connected to the coupling 21 for example, so that the pressure in the passageway 30 is raised and compressed air is blown into the container via the perforation 14' in the belt 6, which is in communication with the passageway 30 on one side and lies over the mouth of the container 5''' on the other side. This is a known procedure in the extraction of gas samples.

The actual gas sample is extracted through the perforation 14, which is connected via the passageway 32 and the duct 37 to the fluid coupling 34, to which an analysing instrument which sucks in the fluid, eg. a mass spectrometer, is connected. Since the container is travelling in the direction of the arrow A at a speed which is equal to the speed of the belt in the direction B, it follows that the perforation 14 travels in step with the container along the entire length of the passageway 32, and gas is extracted from the container during the period they travel together. The same is, of course, true for the other containers which are positioned under one of the other pairs of perforations 15,15' and 16,16', the perforation 15' likewise being in communication with the passageway 30 supplied with compressed air, and the perforation 15 being in communication via the passageway 31 and duct 36 with the fixed fluid coupling 33. A second analysing instrument is connected to the latter. The perforations 16' and 16 are again positioned in the same way as the perforations 14' and 14, so that the first analysing instrument is used again. In this example, therefore, bottles are tested alternately by the first and second analysing instruments as dictated by the arrangement of the perforations. This process continues for further containers which link up with the perforations 13,13', 12,12',11,11', etc as they are carried along.

The containers may be made to connect to the element 6 with the mouth of each container contacting the belt. Alternatively, a clearance may be maintained between the belt and the mouth of the container. "Connection" in the present context therefore does not necessarily imply a fluid tight connection; it merely signifies that the fluid is able to pass from the container to the fixed coupling.

In order to keep the containers and the belt synchronized, the conveyor is provided with a suitable device to maintain a constant interval between containers so that the mouths of the containers keep precisely to the interval between perforations. This device may be eg. a worm conveyor which drives the containers in the region under the apparatus 1. The height of the apparatus above the container conveyor device is made adjustable so that the apparatus can be adapted to different container heights. Furthermore, by exchanging the belt 6, adaptation can be made to different intervals between container mouths, by fitting a belt with perforations spaced accordingly. Should the belt guide element 22 be omitted, as is possible particularly if the distance between the guide pulleys 7 and 8 is short, the fixed couplings 21,33 etc are constructed so that they are in direct contact with the belt and are extended lengthwise in the belt running direction so that the couplings themselves assume the function of the passageway 30,31 etc.

If the apparatus 1 is to be used for inserting a liquid or gas into the bottles, the operation is performed in a similar manner to that already described for the extraction of gas samples. In this case, the fluid to be inserted into the bottles is led from a fluid source eg. to the coupling 21 whence it passes into the passageway 30 and thence through the perforations in the strip-like element 6 into the containers, eg. through the perforation 15 into the container 5''. This takes place during the whole of the travel of the container along the passageway 30.

As has already been stated, a finite length strip could be provided instead of the endless belt 6, eg. in the form of a plastic film wound on a spool, which is run off above the containers in a basically similar fashion, at the same speed as the conveying speed of the containers, and is wound on to another spool after use. Such an arrangement may be useful for specific purposes involving a high risk of contamination, since each perforation (with the corresponding portion of the strip) comes into contact with (or close to) a container only once, so that there is no risk whatever of traces of a substance being transferred by the strip from one container to another. The containers illustrated, which in FIG. 1 are bottles, eg. multi-trip bottles which have been returned and are being inspected prior to refilling, are, of course, intended only as an example. In principle, any kind of container can be connected to a fixed fluid coupling in the manner shown, such as canisters, test tubes, open ampoules, cans, etc.

In FIG. 1 the strip is shown above a linear conveyor line, as will usually be the case. The strip may be a standard commercial belt made of a plastic material; or it may be a thin steel strip which runs eg. over a plastic strip fitted with magnets. Alternatively, the moving strip may for example be constructed as a link belt capable of bending in its longitudinal axis and hence of following a curved conveying path.

FIG. 2 is a side view of an embodiment essentially according to FIG. 1, with the same reference symbols denoting the same parts as in FIG. 1; and FIG. 3 shows a plan view of the passageways in the guide element 22 according to FIG. 1.

Taken in conjunction with FIG. 4, which shows a plan view of a guide element 22', FIG. 2 will now serve to explain a further embodiment with additional couplings 19 and 20. Additionally depicted in FIG. 2, as an example, are ducts 26,27 and 28 connecting the coupling 19 to a passageway in the guide element 22. The duct 27 is stopped with a plug 27'. In this example the passageway is formed as shown in FIG. 4. This passageway which is in communication with the coupling 19 consists of three sections 23,23' and 23''. The passageway which is connected to the coupling 20 via the duct 29 is in this example (as can be seen in FIG. 4) formed as a wide channel 24' which is wide enough to be able to come into contact with several perforations laterally offset from each other.

In this example, there is an additional injection of compressed air via the coupling 19 and the passageways 23,23' and 23''. Compressed air is led via the coupling 21 into a passageway 30'. The coupling 20 is in communication with a partial-vacuum source, so that gas can be extracted from the bottle by way of the passageway 24'. Passageways 31' and 32' are each in communication with an analysing instrument via the fixed couplings 33 and 34 (the link-up of passageways and couplings is not identical with that in the preceding example). The hole pattern of the perforations in the belt 6 is different from that in the preceding example. In FIG. 4 the positions of the perforations 14'' and 14'''; 15'' and 15''', and 16'' and 16''' are shown as black dots. Consequently, gas is sucked out of the bottle 5''' via the passageway 24' (and discharged to atmosphere in the region of the partial-vacuum source) and compressed air is intermittently injected via the passageways 23,23' and 23'''. When the bottle 5''', and hence the perforations 14'' and 14''', come into register with the passageways 30',31' and 32', a steady injection of compressed air occurs via passageway 30' and perforation 14''', and extraction of gas and supply thereof to a first analysing instrument takes place via passageway 32' and perforation 14''. In the case of the bottle 5'', for which the hole pattern of the perforations is as shown at 15'',15''', the compressed air routing is the same, but extraction of gas is effected via passageway 31' to a second analysing instrument. What then happens in the case of the bottle 5' with the perforations 16'' and 16''' is the same as for the bottle 5''' and the perforations 14'' and 14'''. There is thus a continual switching between the two analysing instruments in alternation.

When only one analysing instrument is available for use, eg. when one of the instruments is undergoing maintenance, it is possible, for example, to provide in the guide element 22 a replaceable block 38 which has the duct 36 and a duct 39 in place of 37 (as indicated in FIG. 2); the gas samples from all bottles are then fed to the single analysing instrument at the coupling 33.

The block 38 may also contain eg. fine filters for the ducts 36,37, so that the filters are quickly replaceable. The passageway 24' also has additional lateral branches 24'' which serve to clean the inside of the belt. In the arrangement of passageways in the guide element 22 shown in FIG. 4 as an example, a further passageway 38' is shown, which is in communication with the coupling 39' via the passageway 40'.

These examples clearly show that the link-up between the couplings on the one hand and the perforations or containers on the other hand can easily be modified by reconfiguring or replacing the guide element 22 containing the passageways and/or by corresponding hole patterns of the perforations. There are many other arrangements which can be adopted to meet a specific functional requirement.

FIG. 5 shows a further embodiment of the apparatus 1, likewise with an endless element 6, again in the form of a belt part of which is toothed. The same reference symbols again refer to the same elements as before. However, only part of the apparatus is illustrated, that is to say only one of the end guide assemblies of the belt. At the end guide which is not illustrated, the belt is guided in the same manner as illustrated in the figure. In the illustrated example, the belt is guided at the end shown around two pulleys 8 and 8' arranged one above the other. This pulley arrangement gives a good approach and insertion of the mouthpieces 40,41,42, 43,44 which are provided on the belt in this example and each of which dips into a container. The dipping action facilitates the introduction of fluid into the container or the extraction of fluid from the container. The mouthpieces may be attached to the belt in a releasable manner so that they can be replaced as necessary.

The mouthpieces provided in FIG. 5 are able to dip into the individual containers without contacting them. Other functions, ie. the supply or removal of fluid via the fixed couplings, the ducts in the guide element 22 and the passageways therein leading to the perforations in the belt, or as the case may be to the mouthpieces located at the perforations, are performed in the same way as in the examples which have already been described.

Figure 6:
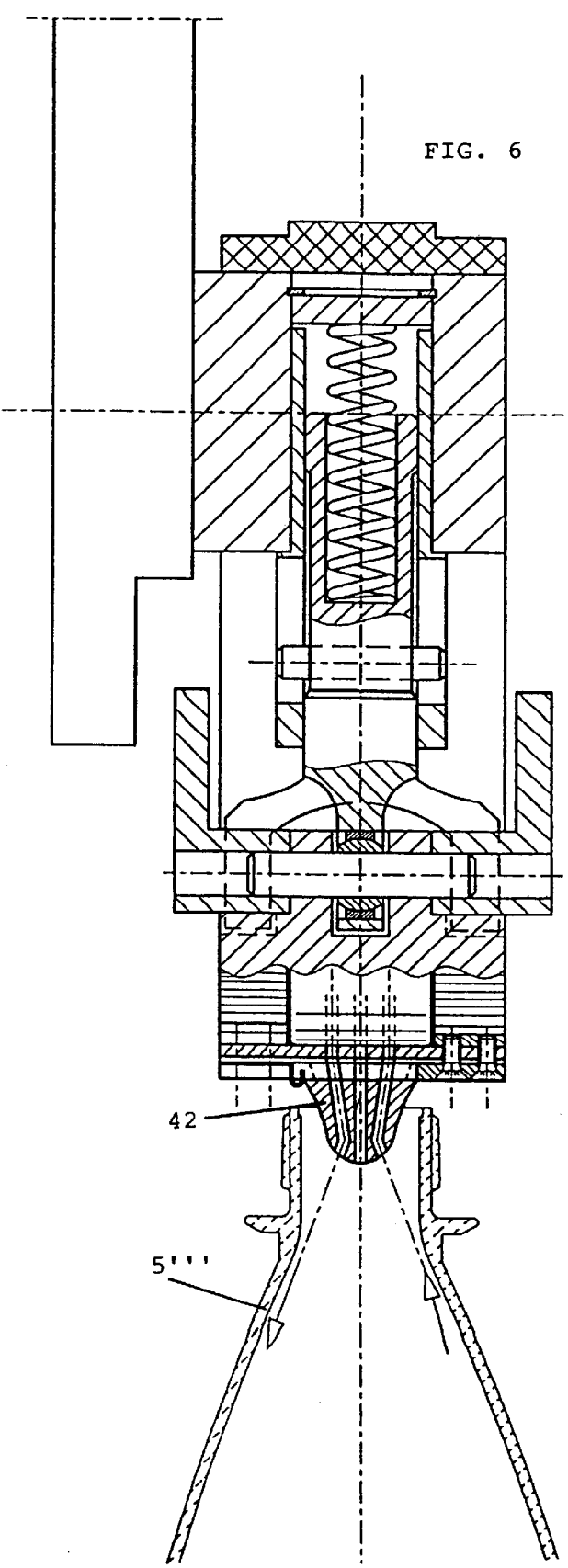
FIG. 6 is a sectioned view of the apparatus of FIG. 5, in the conveying direction.

FIG. 6 shows a sectioned view of an apparatus corresponding to FIG. 5, looking in the conveying direction. In this figure the same reference symbols refer to the same parts as before.

FIG. 7 shows another example of an embodiment of the apparatus in which again, as in the example in FIG. 6, an end guide assembly has two pulleys 8 and 8'. In this embodiment also, six mouthpieces are mounted on the belt. However, these mouthpieces 45,46,47,48, etc are designed to make contact with and seal against the individual bottle mouths. This is illustrated for the mouthpiece 48, which is in contact with the mouth of the container 5. The mouthpieces have a springy construction allowing a corresponding elastic compression of the mouthpiece upon contact with the container mouth. With sealing contact, the containers may for example additionally be tested for leaks. This is done by introducing fluid under pressure into the container, or by withdrawing fluid from the container to create a partial vacuum therein, and by observing the curve of pressure over a certain time in order to detect leaks.

The apparatus 1 is preferably arranged so as to be vertically adjustable over the conveyor path so that it can easily be adapted to the height of the containers. As illustrated eg. in FIG. 2, the guide element 22 can be mounted on sprung bearings 50,51. One effect of this is that the belt 6 can be tensioned as it runs over the guide element 22. This guide element is preferably bowed to improve the seal between the inside of the belt and the passageways. The sprung mounting also allows for compression of the springs and hence allows the guide element to be deflected without damage upon the arrival of a bottle with a cap, or a bottle which is too tall. The compression of the springs may be detected by a switch vane 52 and a sensor 53 triggered by the latter, and the apparatus may eg. be stopped, or the offending bottle may be removed from the conveyor path by an ejector system.

I claim:

1. Apparatus for providing fluid connection between at least one fixed fluid coupling and at least one of a plurality of containers transported on a conveyor in a container conveying direction, characterized by a power-driven, endless strip-like element, one side of the element communicates with the fluid coupling and the other side of the element communicates with a container opening, the strip having at least one perforation forming a connection between the fluid coupling and the container opening.

2. Apparatus for according to claim 1, further characterized by a guide element positioned above the container openings, the guide element guiding the strip-like element at least over a portion of its run.

3. Apparatus according to claim 2, wherein the guide element has at least one fluid passageway which extends in a direction parallel to the container conveying direction the at least one fluid passageway in communication with the at least one fluid coupling and bounded on a side facing the conveyor by one side of the strip-like element, the perforation of the strip-like element being located in the region of the at least one fluid passageway.

4. Apparatus according to claim 3, wherein the guide element has at least one cleaning channel extending in a direction across the strip.

5. Apparatus according to claim 2, wherein a portion of the guide element has a convex curvature.

6. Apparatus according to claim 2, further characterized by a spring mounting for supporting and enabling deflection of the guide element.

7. Apparatus according to claim 6, further characterized by an arrangement which transmits a signal upon deflection of the spring-mounted guide element.

8. Apparatus according to claim 2, wherein the guide element includes a replaceable block and has a plurality of ducts leading from the at least one fluid coupling to the at least one fluid passageway, and at least two ducts of the plurality of ducts are located in the replaceable block.

9. Apparatus according to claim 1, wherein the strip and the upper rim of the container are separated by a clearance to provide a fluid connection without physical contact.

10. Apparatus according to claim 1, wherein the strip-like element defines a plurality of mouthpieces to dip into the container opening and each having at least one fluid duct in communication with the perforation.

11. Apparatus according to claim 10, wherein the mouthpieces are each designed to seal against a rim of the container opening.

12. A method of establishing a fluid connection between at least one fixed fluid coupling and at least one container of a plurality of containers transported on a conveyor relative to the fixed fluid coupling and in a conveyor transporting direction, comprising the steps of:

providing an essentially flat, strip-like element with oppositely-disposed sides and at least one perforation extending through the element from one side of the element to the other side of the element;

providing a fixed guide element against the one side of the strip-like element with a groove in registration with the perforation and placing the one side of the strip-like element in communication with the fixed fluid coupling and the other side facing an opening of a container transported on the conveyor; and driving the strip-like element in step with the container with the perforation through the element adjacent the opening of the container to maintain fluid communication between the oppositely disposed sides of the element and the fixed fluid coupling and the container.

13. A method of establishing a fluid connection as defined in claim 12 further including the step of introducing fluid into the container through the fluid connection.

14. A method of establishing a fluid connection as defined in claim 12 further including the step of testing the container for leaks through the fluid connection.

15. A method of establishing a fluid connection between at least one fixed fluid coupling and at least one of a plurality of containers transported on a conveyor, comprising the steps of:

providing an essentially strip-like element with at least one perforation extending through the element from one side to the other;

placing one side of the strip-like element in communication with the fixed fluid coupling and the other side facing an opening of a container transported on the conveyor;

driving the strip-like element in step with container with the perforation through the element adjacent the opening of the container to maintain fluid communication between the fixed fluid coupling and the container; and extracting fluid from the container through the fluid connection.

16. A method of establishing a fluid connection as defined in claim 15 further including the step of introducing fluid into the container through the fluid connection.

17. A method of establishing a fluid connection as defined in claim 15 further including the step of testing the container for leaks through the fluid connection.

\* \* \* \* \*